US006889833B2

(12) United States Patent
Seiler et al.

(10) Patent No.: US 6,889,833 B2
(45) Date of Patent: May 10, 2005

(54) PACKAGED SYSTEMS FOR IMPLANTING MARKERS IN A PATIENT AND METHODS FOR MANUFACTURING AND USING SUCH SYSTEMS

(75) Inventors: Keith Seiler, Issaquah, WA (US); Eric Hadford, Snohomish, WA (US)

(73) Assignee: Calypso Medical Technologies, Inc., Seattle, WA (US)

( * ) Notice: Subject to any disclaimer, the term of this patent is extended or adjusted under 35 U.S.C. 154(b) by 16 days.

(21) Appl. No.: 10/335,067

(22) Filed: Dec. 30, 2002

(65) Prior Publication Data

US 2004/0124105 A1 Jul. 1, 2004

(51) Int. Cl.[7] .............................................. B65D 83/10
(52) U.S. Cl. ....................... 206/370; 206/438; 604/264; 606/185
(58) Field of Search ................................ 206/363, 364, 206/365, 370, 438; 600/3, 7, 423; 604/164.01, 164.11, 185, 264; 606/184, 185, 167, 187, 188

(56) References Cited

U.S. PATENT DOCUMENTS

| 4,642,786 A | 2/1987 | Hansen |
| 5,170,055 A | 12/1992 | Carroll et al. |
| 5,377,678 A | 1/1995 | Dumoulin et al. |

(Continued)

FOREIGN PATENT DOCUMENTS

| EP | 0719420 | 7/1996 |
| EP | 1034738 | 9/2000 |
| FR | 2635259 | 2/1990 |
| WO | WO-96/08208 | 3/1996 |
| WO | WO-9608999 | 3/1996 |
| WO | WO-99/13775 | 3/1996 |
| WO | WO-97/36192 | 10/1997 |
| WO | WO-97/48438 | 12/1997 |
| WO | WO-99/17133 | 4/1999 |
| WO | WO-99/30182 | 6/1999 |
| WO | WO-99/44506 | 9/1999 |
| WO | WO-99/58055 | 11/1999 |
| WO | WO-00/12009 | 3/2000 |
| WO | WO-00/24332 | 5/2000 |
| WO | WO-00/51514 | 9/2000 |
| WO | WO-01/34049 | 5/2001 |
| WO | WO-02/100485 | 12/2002 |

OTHER PUBLICATIONS

PCT International Search Report dated Sep. 24, 2004, PCT Application No. PCT/US03/41156—corresponding to the present application.
PCT International Search Report dated Apr. 13, 2001, PCT Application No. PCT/US00/31673.
PCT International Search Report dated Jul. 3, 2001, PCT Application No. PCT/US00/31667.
PCT International Search Report dated Oct. 8, 2002, PCT Application No. PCT/US02/17876.
PCT International Search Report dated Jan. 24, 2003, PCT Application No. PCT/US02/29390.
PCT Written Opinion dated Jul. 8, 2003, PCT Application No. PCT/US00/31667.
Kelley MD, William E., "Image–Guided Breast Biopsy: The ABBI* System," 1997.
The World's Most Versatile Biopsy System Offered Only by USSC, ABBI* System Features, 1997.

Primary Examiner—Luan K. Bui
(74) Attorney, Agent, or Firm—Perkins Coie LLP (57) ABSTRACT

Packaged systems for implanting a marker in a patient and methods for manufacturing and using such systems. In one embodiment, a packaged system comprises an introducer having a cannula and a stylet configured to be received in the cannula, a marker in the cannula, and a package having a sterile compartment. The marker can have a casing configured to be implanted in a patient and a resonating circuit in the casing. The resonating circuit can comprise a coil configured to wirelessly transmit a target signal in response to a wirelessly transmitted excitation signal. The introducer is contained within the sterile compartment. In another embodiment, the marker is not loaded in the introducer within the compartment of the package.

27 Claims, 7 Drawing Sheets

U.S. PATENT DOCUMENTS

| | | |
|---|---|---|
| 5,425,382 A | 6/1995 | Golden et al. |
| 5,572,999 A | 11/1996 | Funda |
| 5,617,857 A | 4/1997 | Chader |
| 5,622,170 A | 4/1997 | Schulz |
| 5,622,187 A | 4/1997 | Carol |
| 5,630,431 A | 5/1997 | Taylor |
| 5,697,384 A | 12/1997 | Miyawaki |
| 5,724,030 A | 3/1998 | Urbas |
| 5,727,552 A | 3/1998 | Ryan |
| RE35,816 E | 6/1998 | Schulz |
| 5,779,638 A | 7/1998 | Vesely |
| 5,782,775 A | 7/1998 | Milliman |
| 5,797,849 A | 8/1998 | Vesely |
| 5,817,022 A | 10/1998 | Vesely |
| 5,828,770 A | 10/1998 | Leis |
| 5,830,144 A | 11/1998 | Vesely |
| 5,868,673 A | 2/1999 | Vesely |
| 5,868,675 A | 2/1999 | Henrion |
| 5,879,297 A | 3/1999 | Haynor |
| 5,879,357 A | 3/1999 | Heaton |
| 5,902,238 A | 5/1999 | Golden |
| 5,902,310 A | 5/1999 | Foerster |
| 5,907,395 A | 5/1999 | Schulz |
| 5,913,820 A | 6/1999 | Bladen et al. |
| 5,923,417 A | 7/1999 | Leis |
| 5,951,481 A | 9/1999 | Evans |
| 5,987,349 A | 11/1999 | Schulz |
| 6,026,818 A | 2/2000 | Blair |
| 6,061,644 A | 5/2000 | Leis |
| 6,077,258 A * | 6/2000 | Lange et al. ................ 604/264 |
| 6,082,366 A | 7/2000 | Andra et al. |
| 6,094,007 A | 7/2000 | Faul |
| 6,129,658 A | 10/2000 | Delfino |
| 6,140,740 A | 10/2000 | Porat et al. |
| 6,173,715 B1 | 1/2001 | Sinanan |
| 6,203,524 B1 | 3/2001 | Burney et al. |
| 6,210,315 B1 | 4/2001 | Andrews et al. |
| 6,228,049 B1 * | 5/2001 | Schroeder et al. .......... 604/264 |
| 6,239,724 B1 | 5/2001 | Doron et al. |
| 6,241,734 B1 | 6/2001 | Scribner et al. |
| 6,267,760 B1 | 7/2001 | Swanson |
| 6,363,940 B1 * | 4/2002 | Krag .......................... 606/184 |
| 6,385,482 B1 | 5/2002 | Boksberger et al. |
| 6,447,477 B2 * | 9/2002 | Burney et al. ......... 604/164.01 |
| 6,450,937 B1 * | 9/2002 | Mercereau et al. ............ 600/7 |
| 6,474,341 B1 | 11/2002 | Hunter et al. |
| 6,675,810 B2 | 1/2004 | Krag |
| 6,698,433 B2 | 3/2004 | Krag |

* cited by examiner

PACKAGED SYSTEMS FOR IMPLANTING MARKERS IN A PATIENT AND METHODS FOR MANUFACTURING AND USING SUCH SYSTEMS

TECHNICAL FIELD

The following disclosure relates generally to packaged systems for implanting localization markers with wireless signal transmitters in patients.

BACKGROUND

Medical procedures often require locating and treating target areas within a patient. Radiation therapy and many surgical procedures require locating the target with a high degree of precision to limit collateral damage to healthy tissue around the target. It is particularly important to know or estimate the precise location of the target in radiation oncology because it is desirable to limit the exposure of adjacent body parts to the radiation. In applications for treating prostate cancer, for example, the colon, bladder or other body parts of the patient adjacent to the prostate are desirably not impinged by the high-intensity radiation beam. Surgical applications, such as breast surgery and other procedures involving soft tissue, also require knowing the precise location of a target because a lesion is not necessarily fixed relative to external landmarks on the patient.

Many imaging systems have been used to locate areas or particular targets within a body before performing radiation oncology or surgical procedures. Although x-ray, Magnetic Resonance Imaging (MRI), CT, and other imaging techniques are useful to locate targets within the body at the pre-operative stage of a procedure, they are often not suitable or difficult to use in real time during surgery or radiation therapy. For example, the location of a lesion in soft tissue or an organ within the patient's body may shift relative to external landmarks on the patent between the pre-operative imaging procedure and the actual radiation or surgical procedure. Additionally, when imaging systems are used during a radiation or surgical procedure, they may not provide sufficiently accurate measurements of the location of the lesions and they may interfere with the radiation or surgical procedure. Therefore, imaging techniques by themselves are not suitable for accurately identifying the actual location of a target for many medical applications.

Another technique to locate a target in a patient is to implant a marker relative to the target. For example, implantable markers that generate a signal have been proposed for use to locate a selected target in a patient in radiation oncology procedures. U.S. Pat. No. 6,385,482 B1 issued to Boksberger et al. (Boksberger) discloses a device having an implanted emitter unit located inside or as dose as possible to a target object and a plurality of receiver units that are located outside of the patient. Boksberger discloses determining the location of the target object by energizing the emitter unit using a generator and sensing the signal from the emitter unit with the receiver units. Boksberger discloses and claims that the receiver units are configured to determine the gradient of the magnetic field generated by the emitter unit. Boksberger discloses emitter units that are energized using a wired connection to the external generator. Boksberger also indicates that it is conceivable to use an emitter unit that is energized by a battery or excited by an electromagnetic field generated by the external generator. The wired emitter units disclosed in Boksberger, however, may not be suitable for use in radiation oncology and many surgical procedures because it is impractical to leave a wired emitter unit implanted in a patient for the period of time of such procedures (e.g., five to forty days).

Another technique to locate a target in a patient is to implant passive, gold fiducials in or near the target site. The positions of the gold fiducials are determined periodically using radiation. Although gold fiducials are useful for localizing a target within a patient, these systems do not provide sufficiently accurate real time measurements of the target site location during radiation oncology procedures.

One practical difficulty of using wired markers or gold fiducials is implanting the objects in the patient. Boksberger, for example, discloses positioning the emitter unit at a desired site in the body by percutaneously inserting a hollow puncture needle into the patient and then passing a tube through the hollow puncture needle. After the tube is in place, Boksberger further discloses passing the emitter unit through the tube to position the emitter unit at or near the target within the patient. This is a cumbersome process because a tube is left in the patient during the radiation procedure to provide a passageway to remove the leads and the emitter unit. Moreover, the emitter units must be loaded into the tubes by skilled personnel at the healthcare provider. Thus, wire markers is cumbersome, inefficient, and not well suited for radiation oncology applications that require a patient to return for treatments over a period of five to forty days.

Figure 1A:
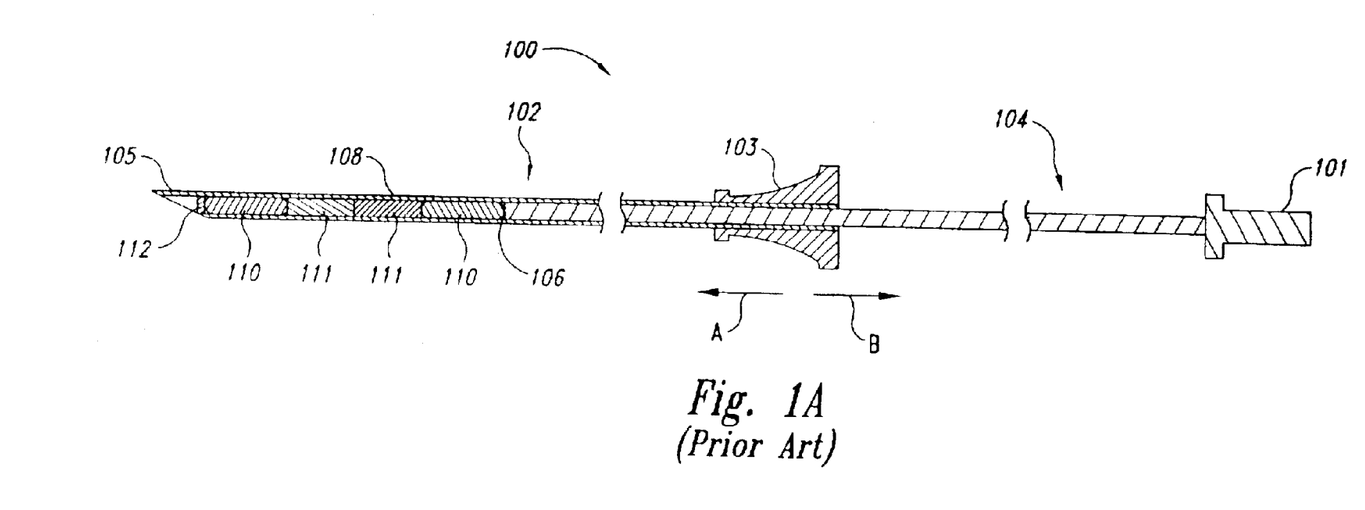
FIGS. 1A and 1B are cross-sectional views of a two-piece introducer of the prior art used for implanting radioactive seeds in brachytherapy.
Figure 1B:
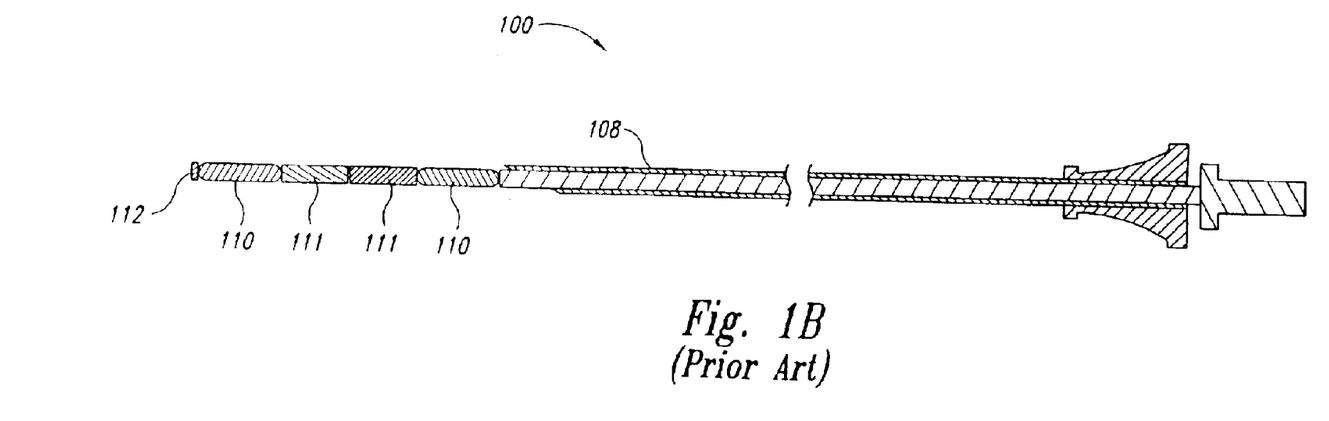

Another process for percutaneously implanting objects in a patient is brachytherapy for treating prostate cancer. In brachytherapy, radioactive sources or "seeds" are implanted relative to a tumor to provide a high dose of radiation to the tumor, but not the healthy tissue surrounding the tumor. FIGS. 1A and 1B are cross-sectional views of a two-piece introducer 100 of the prior art used in brachytherapy. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a cannula 108 extending through the second handle 103. The cannula 108 is configured to hold radioactive seeds 110 or other objects. The cannula 108 has a distal tip 105 configured to percutaneously penetrate the patient for implantation of the seeds 110 in the patient. Inert spacers 111 can be used to provide the desired spacing between the seeds 110 when they are implanted in the patient. The seeds 110 and spacers 111 are retained in the cannula 108 by a plug 112 made from bone wax or other suitable bio-compatible materials.

To implant the desired arrangement of seeds 110 at a target location in a patient, an operator pushes the cannula 108 in a first direction (arrow A) to insert the tip 105 into the patient. The operator then pushes the second handle 103 further in the first direction to position the tip 105 at the desired depth within the patient where the seeds 110 are to be implanted. Throughout this motion, the operator moves the needle 102 and the stylet 104 together as a unit. At the desired depth, the operator grasps the first handle 101 with one hand and the second handle 103 with the other hand. At this point, the operator attempts to hold the first handle 101 stationary while simultaneously sliding the second handle 103 back in a second direction (arrow B) toward the first handle 101. As shown in FIG. 1B, this movement causes the cannula 108 to slide over the seeds 110 and the spacers 111 to implant them in the patient. In many situations, however, the operator moves the first handle 101 in the first direction (arrow A) while sliding the second handle 103 back in the second direction (arrow B). This causes the stylet 104 to push the seeds 110 out of the cannula 108, which can cause the seeds 110 to move laterally away from the axis of the cannula (i.e., a "train wreck"). Thus, one concern of the prior art introducer 100 is misplacement of the seeds 110.

Another concern of the prior art introducer 100 used in brachytherapy applications is that a skilled operator typically loads a specific pattern of seeds and spacers into an introducer at the facility of a healthcare provider according to the specific needs of each particular patient. In most brachytherapy applications it is necessary to arrange the seeds and spacers at the hospital or clinic according to the specific parameters of each patient because the location and shape of the tumors vary among different patients. Arranging and loading the seeds for each patient is a time consuming process that requires skilled personnel and is subject to human error. Therefore, the techniques for inserting or implanting objects in the patients used in brachytherapy are not desirable in other applications.

DETAILED DESCRIPTION

The following disclosure describes medical devices and methods related to packaged systems for implanting a marker in a patient. Certain specific details are set forth in the following description and in FIGS. 2A–7 to provide a thorough understanding of various embodiments of the invention. It will be appreciated that other embodiments in accordance with the invention can include additional or different features than those shown in 2A–7. Several other embodiments of packaged systems for implanting a marker in a patient in accordance with the invention do not include some of the features shown in these figures. Additionally, for purposes of clarity, like reference numbers refer to similar or identical components.

Figure 2A:
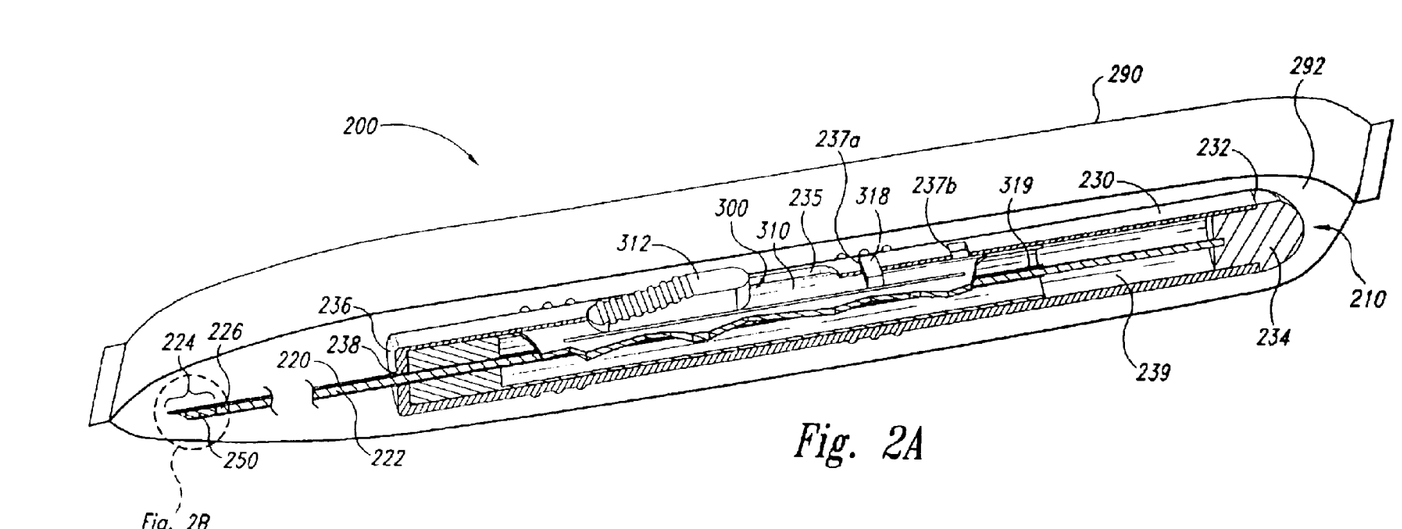
FIG. 2A is a cut-away isometric view of a packaged system for implanting a marker in a patient in accordance with one embodiment of the invention.

FIG. 2A is a cut-away isometric view of a packaged system 200 for implanting a marker in a patient. In this embodiment, the packaged system 200 includes an introducer 210 having a cannula 220 and a stylet 222 configured to be received in the cannula 220. The packaged system 200 can also include a marker 250 in the cannula 220. The marker 250 has a casing configured to be implanted in a patient and a resonating circuit in the casing. The resonating circuit comprises a coil configured to wirelessly transmit a target signal in response to a wirelessly transmitted excitation signal. The packaged system 200 further includes a package 290 having a sterile compartment 292 in which the introducer 210 and the marker 250 are contained. In this embodiment, the package 290 is a sealed pouch or envelope, but it can be an enclosed tray or other structure in other embodiments. Several features of the introducer 210 and the marker 250 will be described with reference to FIGS. 2A–4B.

The introducer 210 can include a handle 230 and an actuator assembly 300 in the handle 230. The handle 230 has a proximal end 232 with a plug 234 and a distal end 236 with an opening 238. The handle 230 can also include a longitudinal slot 235 along the top surface in which a button 312 of the actuator assembly 300 can move. The handle 230 can also include notches 237a and 237b for receiving a tab 318 of the actuator assembly 300. The interaction between the handle 230 and the actuator assembly 300 is described in more detail below. The handle 230 also has a cavity 239 for receiving a portion of the cannula 220 and a portion of the stylet 222.

The stylet 222 can have a proximal end positioned in the cavity 239 of the handle 230 and a distal end projecting out through the opening 238 of the handle 230. In this embodiment, the proximal tip of the stylet 222 is fixedly attached to the plug 234 so that the stylet 222 does not move relative to the handle 230. The cannula 220 has a lumen that receives a portion of the stylet 222. In several embodiments, the cannula 220 is not fixedly attached to the handle 230. As such, the cannula 220 can not only slide over the stylet 222, but also through the opening 238 of the handle 230. The cannula 220 slides between a storage position (shown in FIG. 2A) and a release position. The marker 250 is contained within a distal portion 224 of the cannula 220 in the storage position, but the marker 250 is expelled from the cannula 220 in the release position. As such, at least a length of the distal portion 224 of the cannula 220 slides over a distal tip 226 of the stylet 222 as the marker 250 is implanted in the patient.

Figure 2B:
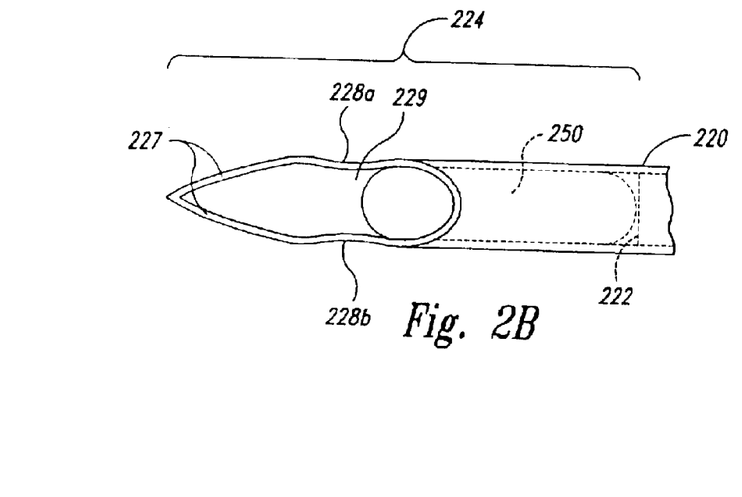
FIG. 2B is a plan view showing a portion of the packaged system in greater detail.

FIG. 2B is a plan view illustrating one embodiment of the distal portion 224 of the cannula 220 in greater detail. In this embodiment, the distal portion 224 has a beveled cutting edge 227 and a plurality of protrusions 228a and 228b projecting radially inwardly into a lumen 229 of the cannula 220. The protrusions 228a and 228b are diametrically opposed across the lumen 229. In other embodiments, the cannula 220 can have only a single projection 228 on one side of the lumen 229. In either case, the protrusions are only slightly smaller than the outside diameter of the marker 250. The protrusions provide tactile feedback to the operator as the cannula 220 retracts over the stylet 222. Such tactile feedback provides an indication to the operator that the marker 250 has been released within the patent. This feature can be particularly useful when the introducer 210 is used to sequentially implant a plurality of markers from the same introducer at different depths or locations within the patient. Additionally, the protrusions retain the marker 250 within the cannula 220 for shipping and storage. One advantage of the protrusions is that they are not susceptible to fluctuations in temperatures so that the preloaded introducers can be shipped and stored in hot environments.

Figure 3A:
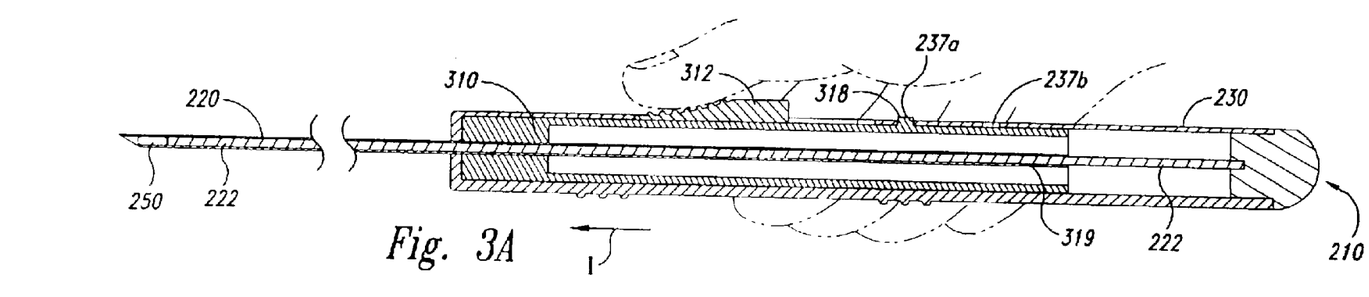
FIGS. 3A–3C are cross-sectional views illustrating the operation of an introducer for use in the packaged system in accordance with an embodiment of the invention.
Figure 3B:
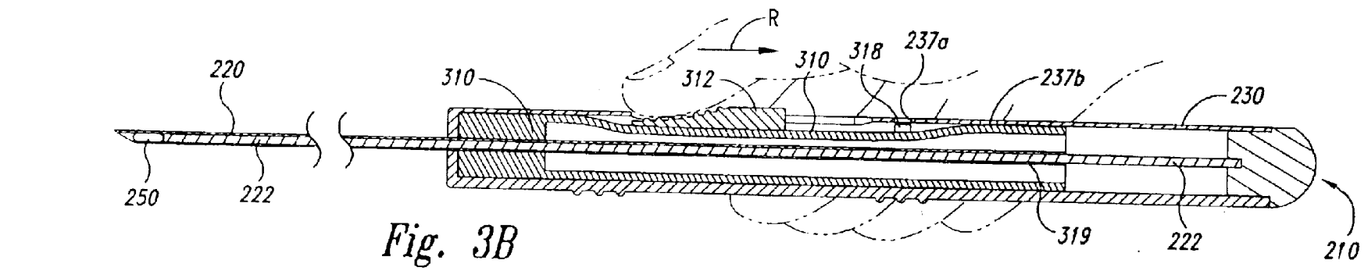
Figure 3C:
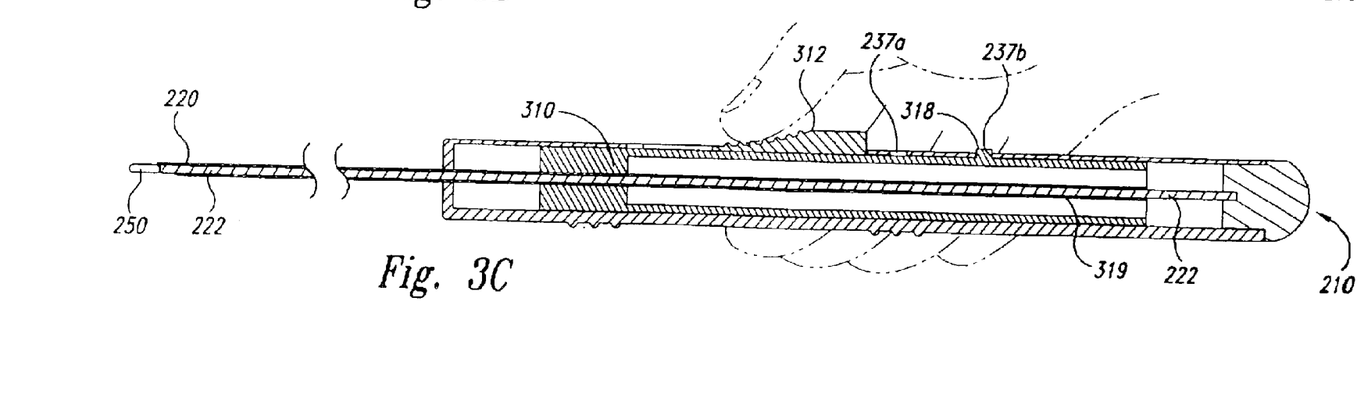

FIGS. 3A–3C are cross-sectional views illustrating the interaction between the handle 230 and the actuator assembly 300 in the operation of the introducer 210. The actuator assembly 300 can include a slider 310 that is fixedly attached to the cannula 220 and slidably received in the handle 230. The slider 310, for example, can be an assembly including the button 312, the tab 318, and a flange 319. The button 312 is slidably received in the slot 235 of the handle 230 and the flange 319 is fixed to a proximal end of the cannula 220. The tab 318 can be positioned in the first notch 237a of the handle 230 in the storage position or the second notch 237b of the handle 230 in the release position.

FIG. 3A illustrates an initial stage of a method for implanting the marker 250 in a patient. At this stage an operator grips the handle 230 to move the button 312 using a digit and inserts the cannula 220 into the patient (arrow I). The operator then pushes the button 312 downward to disengage the tab 318 from the first notch 237a in the handle 230 and slides the actuator assembly 300 in the proximal direction as shown in FIG. 3B (arrow R). The operator continues to move the slider 310 proximally until the tab 318 engages the second notch 237b to define the release position as shown in FIG. 3C. The axial movement of the actuator assembly 300 moves the cannula 220 axially over the stylet 222 because the cannula 220 is fixedly attached to the flange 319. The marker 250 is implanted in the patient when the actuator assembly 300 is in the release position.

Figure 4A:
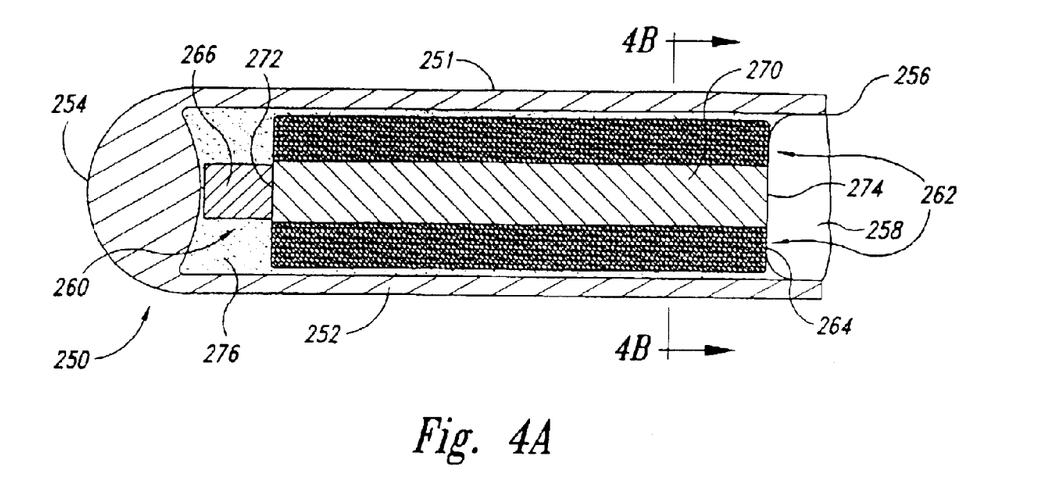
FIG. 4A is a cross-sectional view taken along a longitudinal axis of a marker for use in a packaged system in accordance with an embodiment of the invention.
Figure 4B:
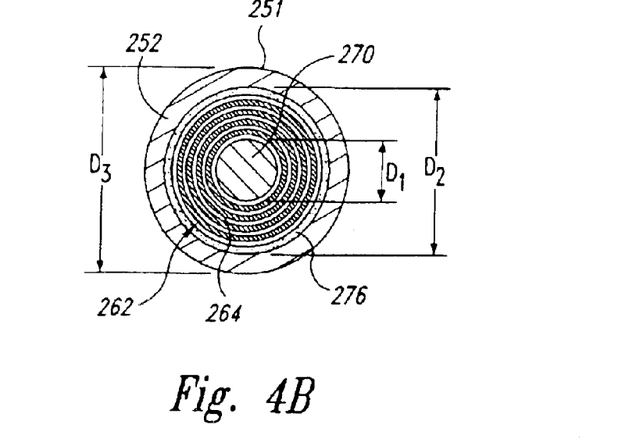
FIG. 4B is a cross-sectional view in a plane 4B—4B normal to the longitudinal axis of the marker shown in FIG. 4A.

FIGS. 4A and 4B are cross-sectional views illustrating an embodiment of the marker 250 that can be loaded into the cannula 220 and packaged in the package 290 in accordance with an embodiment of the invention. The marker 250 can include a casing 251 formed from a bio-compatible barrier and configured to be implanted in the patient or otherwise attached to the patient. The casing 251 can be a generally symmetrical capsule at a size to fit within a 14-gauge cannula for percutaneous implantation, but the casing 251 can have other configurations and be larger or smaller. The casing 251, for example, can have barbs to anchor the casing 251 in soft tissue. In one embodiment the casing 251 includes (a) a glass capsule or shell 252 having a closed end 254 and an open end 256, and (b) a sealant 258 in the open end 256 of the shell 252. The casing 251 and sealant 258 can be made from plastics, ceramics, glass or other suitable bio-compatible materials.

The marker 250 can include a resonating circuit 260 in the casing 251. The resonating circuit 260 produces a wirelessly transmitted target signal in response to a wirelessly transmitted excitation signal. In one embodiment, the resonating circuit 260 comprises a coil 262 having a plurality of windings of a conductor 264. The conductor 264 of the illustrated embodiment can be hot air or alcohol bonded wire having a gauge of approximately 45–52 gauge. The coil 262 can have 800–2000 turns, and the turns are preferably wound in a tightly layered coil. Many embodiments of the resonating circuit 260 also include a capacitor 266 electrically coupled to the coil 262. The coil 262 by itself, or the combination of the coil 262 and the capacitor 266, effect a signal transmitter that resonates at the selected frequency. The signal transmitter, for example, generates an alternating magnetic field at the selected resonant frequency in response to an excitation signal.

The resonating circuit 260 is powered by a wirelessly transmitted excitation signal such that the resonating circuit is a leadless circuit (i.e., not connected to external lead wires that extend through or project from the casing 251). In one embodiment, the excitation signal that energizes the resonating circuit 260 is an alternating excitation magnetic field generated externally with respect to the patient. The excitation signal can have a frequency that matches the resonant frequency of the resonating circuit 260. In response to the excitation field, the resonating circuit 260 produces a target signal or response signal that can be measured by a sensor array positioned externally with respect to the patient. Suitable devices for generating the magnetic excitation field and sensing the target signal are disclosed in U.S. patent application Ser. Nos. 10/027,675 filed on Dec. 20, 2001; Ser. No. 10/044,056 filed on Jan. 11, 2002; and Ser. No. 10/213,980 filed on Aug. 7, 2002, which are herein incorporated by reference.

The marker 251 further includes a ferromagnetic element 270 having a first end 272 and a second end 274. The ferromagnetic element 270 is at least partially surrounded by the coil 262. In the particular embodiment shown in FIG. 4A, the coil 262 surrounds the ferromagnetic element 270 from the first end 272 to the second end 274. In other embodiments, the coil 262 surrounds only a portion of the ferromagnetic element 270. The capacitor 266 can be positioned at the first end 272 of the ferromagnetic element 270. Additionally, the resonating circuit 260 and the ferromagnetic element 270 can be fixed to the casing 251 by an adhesive 276.

The ferromagnetic element 270 is preferably composed of ferrite or other materials that have high magnetic permeability compared to free space. The amount of energy that the inductor is capable of storing is limited, in part, by the magnetic field saturation of the ferromagnetic element 270. Although it has been understood that the size of the ferromagnetic material should be maximized within the limited space of the marker, the volume of the ferromagnetic element 270 in the particular embodiment of the marker 250 shown in FIG. 4A is significantly less than the available volume within the casing 251. The smaller volume of the ferromagnetic element 270 reduces the force exerted on the marker 251 when it is placed in a magnetic resonance imaging device having a field strength of 1.5 T including a corresponding gradient field of approximately 3 T/m. In one embodiment, the ferromagnetic element has a volume such that when the marker is in a magnetic resonance device, then the force exerted on the marker by the magnetic field is less than gravitational force exerted on the marker. Additionally, the small volume of the ferromagnetic element 270 reduces the size of the artifact in an image from a magnetic resonance device. It will be appreciated that ferromagnetic materials will produce an artifact (i.e., a region in which image information is suppressed) in an image produced by a magnetic resonance imaging device. The volume of the ferromagnetic element 270 can be reduced to a size such that it produces a small artifact in an image from a magnetic resonance device. In general, such ferromagnetic elements 270 have small diameters less than the size of commercially available ferrite rods for transponder applications (i.e., 0.75 mm diameter ferrite rods available from Ferroxcube of Spain).

FIG. 4B is a cross-sectional view of the marker 251 taken along line 4B—4B of FIG. 4A. In one embodiment, the ferromagnetic element 270 is a ferrite rod having a diameter $D_1$ of approximately 0.20–0.70 mm, but the ferromagnetic element 270 can have other cross-sectional configurations in other embodiments. For example, an extruded ferrite rod can have an elliptical, oval or polygonal cross section. The ferromagnetic element 270 can have a length of approximately 2.0–20 mm. In one particular embodiment the ferromagnetic element 270 has a diameter of approximately 0.25–0.50 mm and a length of 2–12 mm, and in another embodiment the ferromagnetic element 270 has a diameter of 0.30–0.35 mm and a length of 4.0–6.0 mm. The coil 262 has an inner diameter of approximately 0.20–0.80 mm and an outer diameter $D_2$ of approximately 0.6–1.4 mm or 0.8–1.9 mm. The casing 251 can have an outer diameter $D_3'$ of approximately 1.0–3.0 mm. In other embodiments, the coil 262 can have different inner and outer diameters, and the casing 251 can have a different outer diameter. In another particular embodiment, the diameter $D_1$ of the ferromagnetic element 270 is approximately 0.30–0.50 mm, the inner diameter of the coil 262 is approximately 0.30–0.60 mm, the outer diameter $D_2$ of the coil 262 is approximately 1.2–1.9 mm (or 1.2–1.4 mm), and the outer diameter $D_3$ of the casing 251 is approximately 1.8–2.0 mm. The volume of the ferromagnetic element 270 can be approximately 0.35–19.0 $mm^3$.

Referring back to FIG. 2, the packaged system 200 is useful for storing preloaded introducers that contain resonating markers used to identify the location of a target within a patient. In operation, a user can open the package 290 and remove the preloaded introducer 210. The user then percutaneously inserts the cannula 220 and stylet 222 into the patient using image guided techniques to locate the marker 250 at a desired location within the patient. As explained above, the operator then moves the actuator assembly 300 in a proximal direction to retract the cannula 220 and release the marker 250 at the desired location within the patient.

One advantage of the packaged system 200 is that the markers 250 are preloaded in the introducer 210 and stored in a sterile compartment 292 to provide a more efficient product to healthcare providers. The markers can be preloaded in the introducer because this application is directed toward markers that are energized by a wirelessly transmitted magnetic field and produce a wirelessly transmitted target signal. It is more difficult to preload wired markers because the introducer must accommodate the external leads attached to the marker. Moreover, unlike brachytherapy applications that require custom configuration of the seeds in an introducer, applications for using a wireless marker do not require a custom configuration of the marker relative to the introducer. As such, the aspect of preloading a marker in an introducer and packaging the introducer in a sterile compartment is not useful for implanting the objects of the prior art for use in their intended purposes.

The packaged system 200 illustrated in FIG. 2A can have several different embodiments. For example, a plurality of markers 250 can be preloaded into the cannula 220, and the markers can have the same frequency or the markers can have different frequencies. In another embodiment, the packaged system 200 can have a plurality of markers in the cannula and spacers positioned between the markers. The spacers provide a known linear distance between the markers to enhance the accuracy with which the markers can be implanted in a patient. Other embodiments of the packaged system 200 have a container including a tray with a retainer for holding the introducer and a cover sealed to the tray. Additionally, the stylet 222 can be inserted in the cannula 220 as shown in FIG. 2A, but in still other embodiments the stylet 222 is separate from the cannula 220 within the package 290.

Figure 5:
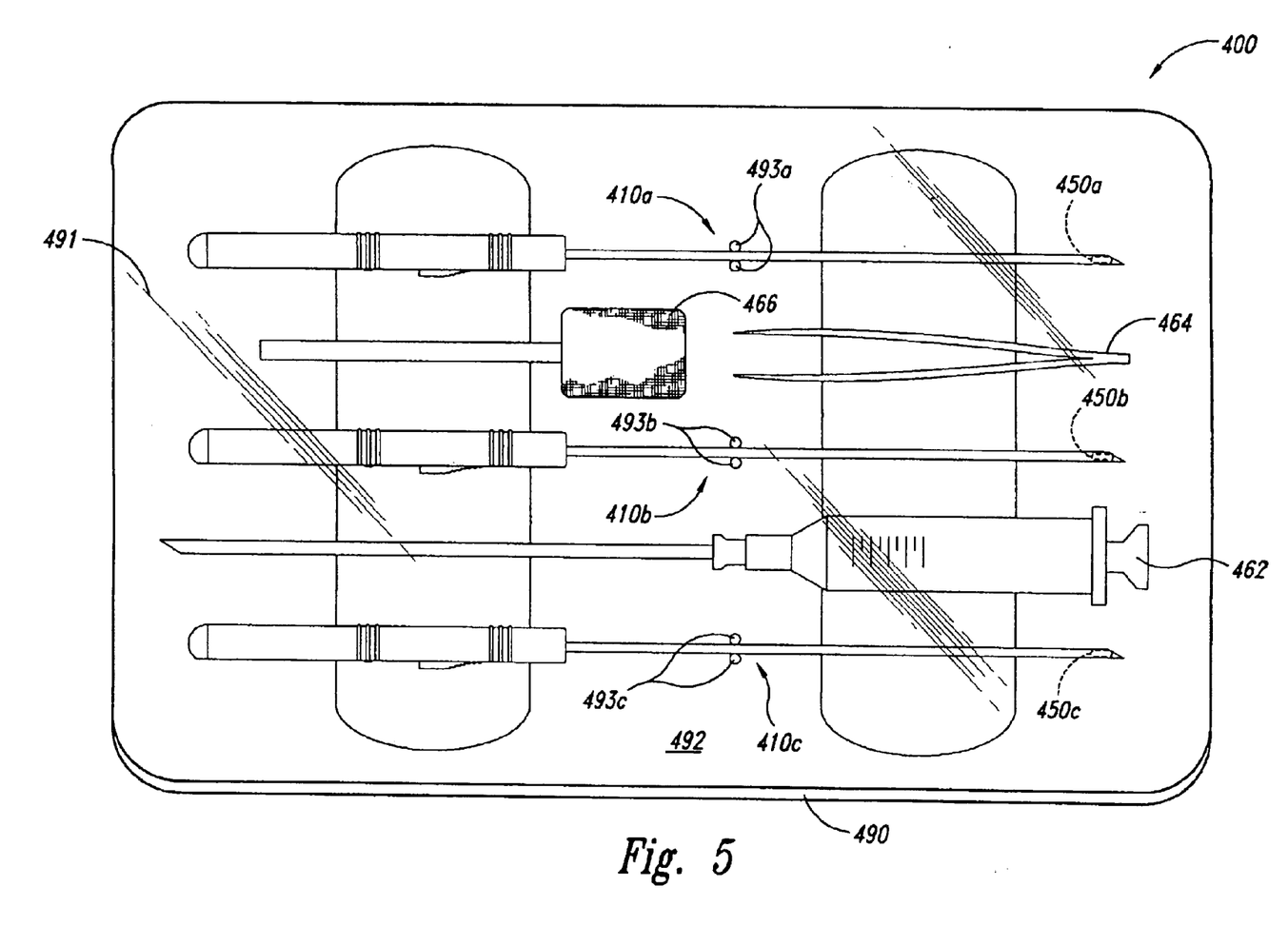
FIG. 5 is a plan view of a packaged system for implanting a marker in a patient in accordance with another embodiment of the invention.

FIG. 5 is an isometric view of a packaged system 400 for implanting a marker in a patient in accordance with another embodiment of the invention. In this embodiment, the packaged system 400 includes a plurality of introducers 410 (identified individually by reference numbers 410a–c) and a plurality of markers 450 (identified individually by reference numbers 450a–c). A first marker 450a is loaded in the first introducer 410a, a second marker 450b is loaded in the second introducer 410b, and a third marker 450c is loaded in the third introducer 410c. The introducers 410a–c and the markers 450a–c can be substantially similar or identical to the introducer 210 and the marker 250, respectively, described above with reference to FIG. 2A. A number of additional items, such as a syringe 462, tweezers 464 and a swab 466 can also be included in the packaged system 400.

The packaged system 400 further includes a package having a tray 490 and a cover 491 sealably attached to the tray to create a compartment 492. The tray 490 can further include a plurality of introducer retainers 493 (identified individually by reference numbers 493a–c) that retain the introducers 410a–c, respectively. The retainers 493 can be molded projections that grip the cannulas or the handles of the introducers 410, or the retainers 493 can be depressions in the tray 490 or cover 491 configured to conform to the contour of the introducers 410a–c.

The introducers 410 can be loaded with markers that transmit different target signals. For example, the first marker 450a can be configured to wirelessly transmit a first target signal at a first frequency in response to a first excitation signal; the second marker 450b can be configured to wirelessly transmit a second target signal at a second frequency in response to a second excitation signal; and the third marker 450c can be configured to wirelessly transmit a third target signal at a third frequency in response to a third excitation signal. The markers 450a–c can have the same frequency in other embodiments.

Figure 6:
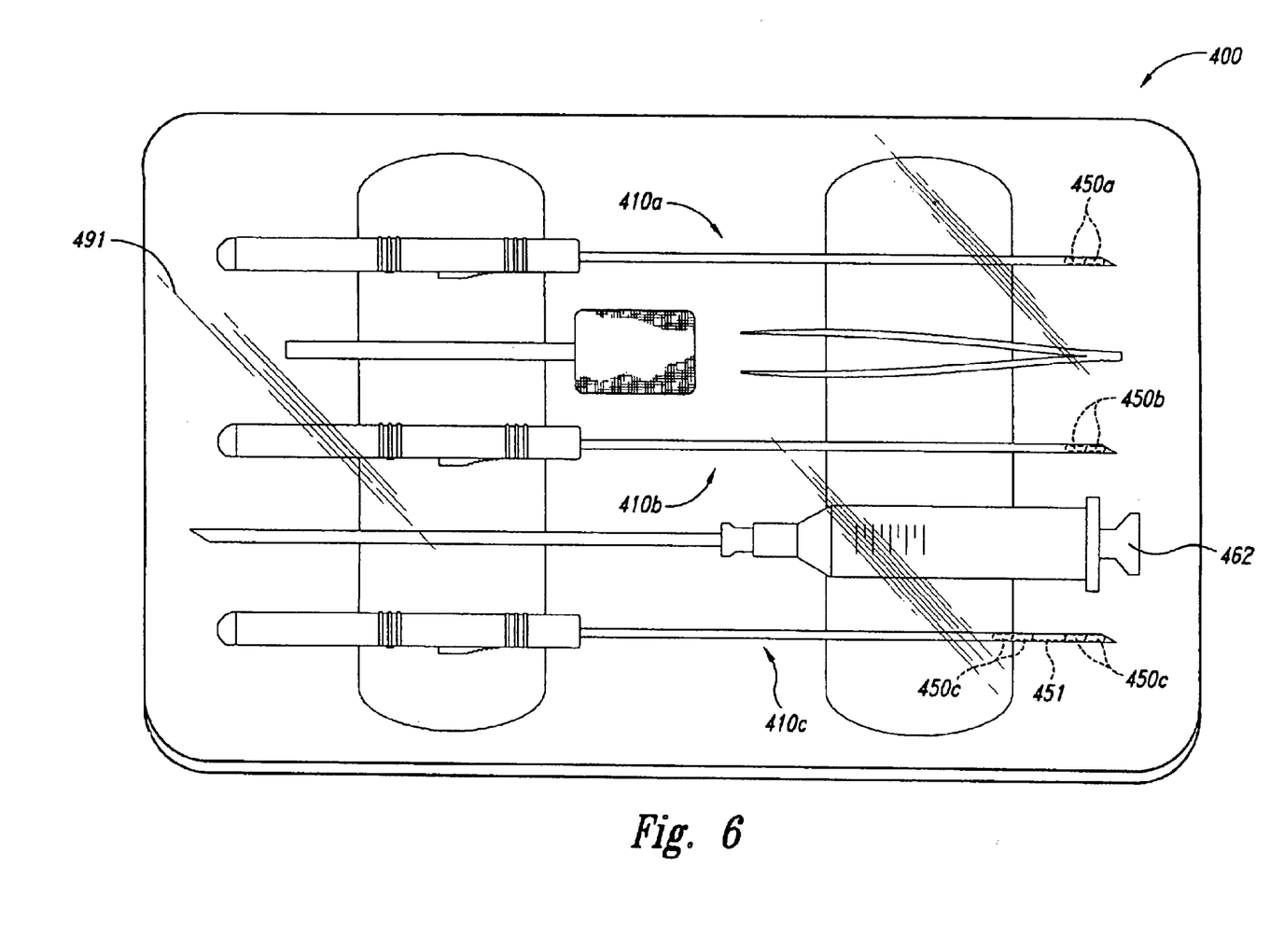
FIG. 6 is a plan view of a packaged system for implanting a marker in a patient in accordance with another embodiment of the invention.

FIG. 6 is an isometric view illustrating another embodiment of the packaged system 400. In this embodiment, the first introducer 410a is loaded with a plurality of first markers 450a, the second introducer 410b is loaded with a plurality of second markers 450b, and the third introducer 410c is loaded with a plurality of third markers 450c. The markers 450a–c can be configured to transmit target signals having different frequencies as explained above with reference to FIG. 5. In another embodiment, one or more of the introducers 410 can include a spacer between two markers. Referring to the third introducer 410c in FIG. 6, for example, a spacer 451 can be placed between one or more of the markers 450c to provide a known lineal spacing between a group of markers that is to be implanted relative to a target site in a patient.

Figure 7:
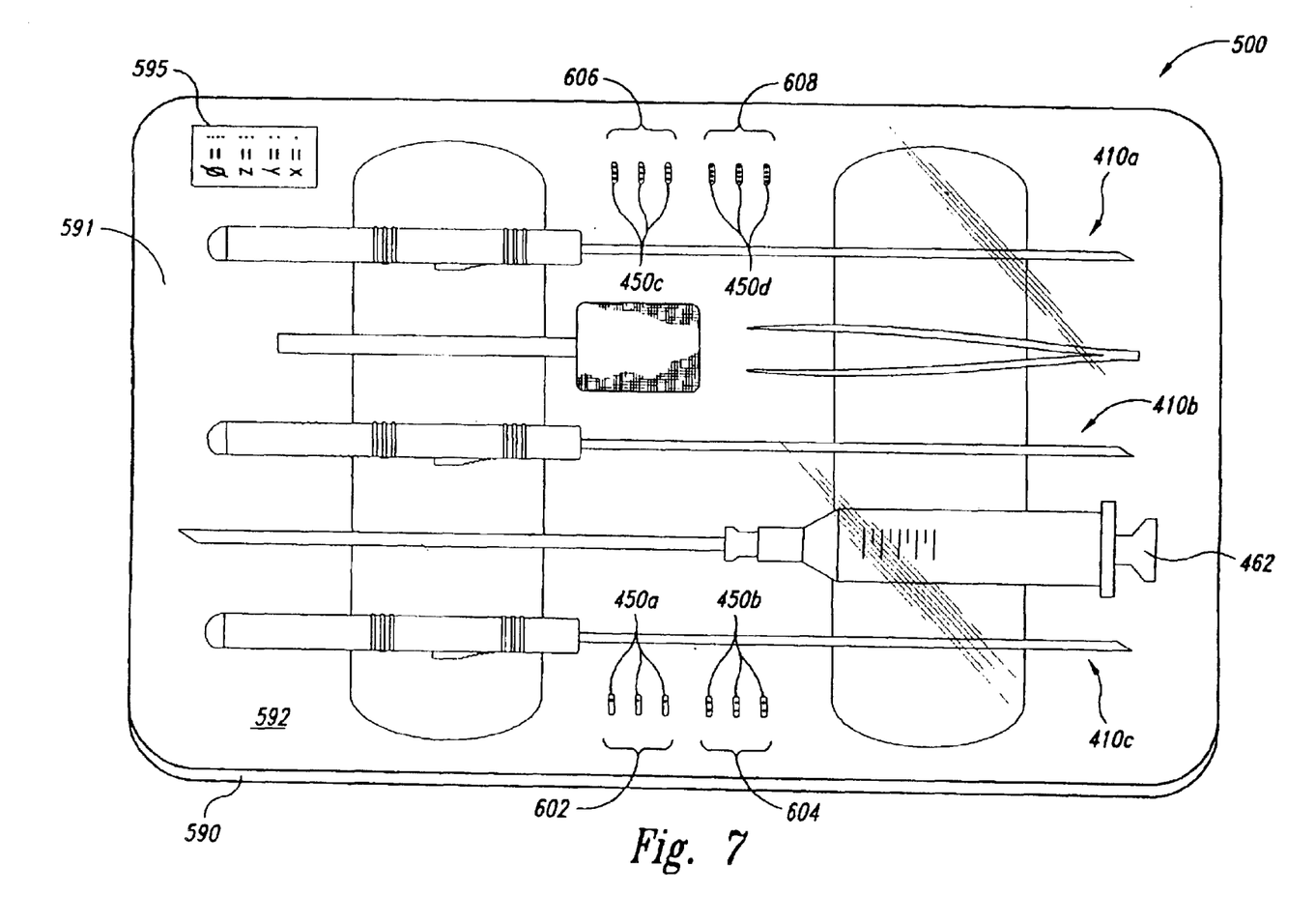
FIG. 7 is a plan view of a packaged system for implanting a marker in a patient in accordance with another embodiment of the invention.

FIG. 7 is an isometric view of a packaged system 500 in accordance with another embodiment of the invention. In this embodiment, the packaged system 500 can include a plurality of the introducers 410a–c and a plurality of the markers 450a–d. The packaged system 500 is different from the packaged system 400 in that the markers 450 are not preloaded into the introducers 410. The packaged system 500 can include a tray 590 and a cover 591 sealed to the tray to form a sealed, sterile compartment 592. The tray 590 can have a plurality of retainers, such as depressions, to hold the introducers 410 and the markers 450. The retainers for the markers 450 can be small depressions that are shaped slightly larger than the markers. The markers 450 can include a first set 602 of first markers 450a, a second set 604 of second markers 450b, a third set 606 of third markers 450c, and a fourth set 608 of fourth markers 450d. The first markers 450a can wirelessly transmit a first signal at a first frequency, the second markers 450b can wirelessly transmit a second wireless signal at a second frequency, the third markers 450c can wirelessly transmit a third signal at a third frequency, and the fourth markers 450d can wirelessly transmit a fourth signal at a fourth frequency. The packaged system 500 can have other embodiments with a different number of introducers and markers. For example, the packaged system 500 can include only a single introducer and three unloaded markers that have different frequencies. As such, the packaged system 500 is not limited to the particular configuration shown in FIG. 7.

The particular markers can include indicia, such as dots, colors, lines or text, that indicate the actual frequency or provide an indicator of the frequency. The indicia can be markings that are correlated with a legend 595 to determine the actual frequency X, Y, Z or Q of a particular marker. In operation, the markers can be loaded into the introducers after the cover 591 has been removed from the tray 590. The packaged system 500 accordingly requires the operator to perform the extra procedures of loading the markers into the introducers.

From the foregoing, it will be appreciated that although embodiments of the item matching system have been described for purposes of illustration, various modifications may be made without deviating from the spirit and scope of the invention. Accordingly, the invention is not limited except by the appended claims.

We claim:

1. A packaged system for implanting a marker in a patient, comprising:
   a package having a sterile compartment;
   an introducer in the sterile compartment, the introducer having a cannula and a stylet configured to be received in the cannula; and
   a marker having a casing and a resonating circuit in the casing, the casing being configured to be implanted in a patient, and the resonating circuit comprising a coil configured to wirelessly transmit a target signal in response to a wirelessly transmitted excitation signal, wherein the marker is preloaded in the cannula of the introducer or retained within the sterile compartment outside of the cannula.

2. The packaged system of claim 1 wherein the marker 0 comprises a first marker and the system further comprises a second marker, the first and second markers being preloaded in the cannula, and wherein the second marker comprises another casing configured to be implanted in the patient and another resonating circuit that wirelessly transmits another target signal in response to another wirelessly transmitted excitation signal.

3. The packaged system of claim 1 wherein:
   the marker comprises a first marker, the casing comprises a first casing, and the resonating circuit comprises a first resonating circuit configured to wirelessly transmit a first target signal at a first frequency in response to a first excitation signal; and
   the system further comprises a second marker having a second casing and a second resonating circuit in the second casing, the second resonating circuit being configured to wirelessly transmit a second signal at a second frequency in response to a second excitation signal, wherein the first frequency is different than the second frequency.

4. The packaged system of claim 1 wherein the marker is the sole marker in the cannula.

5. The packaged system of claim 1 wherein:
   the introducer comprises a first introducer and the marker comprises a first marker positioned in the first introducer, the casing comprises a first casing, and the resonating circuit comprises a first resonating circuit configured to produce a wirelessly transmitted first target signal in response to a first excitation signal; and
   the system further comprising a second introducer in the package and a second marker in the second introducer, the second marker comprising a second casing configured to be implanted in the patient and a second resonating circuit in the second casing, and the second resonating circuit being configured to wirelessly transmit a second target signal in response to a second excitation signal.

6. The packaged system of claim 5 wherein the package comprises a tray and a cover sealed to the tray, the tray having a first introducer retainer in which the first introducer is positioned and a second introducer retainer in which the second introducer is positioned.

7. The packaged system of claim 1 wherein:
   the introducer comprises a first introducer and the marker comprises a first marker positioned in the first introducer, the casing comprises a first casing, and the resonating circuit comprises a first resonating circuit configured to produce a wirelessly transmitted first target signal at a first frequency in response to a first excitation signal; and
   the system further comprising a second introducer in the package and a second marker in the second introducer, the second marker comprising a second casing configured to be implanted in a patient and a second resonating circuit in the second casing, and the second resonating circuit being configured to wirelessly transmit a second target signal at a second frequency in response to a second excitation signal.

8. The packaged system of claim 7 wherein the package comprises a tray and a cover sealed to the tray, the tray having a first introducer retainer in which the first introducer is positioned and a second introducer retainer in which the second introducer is positioned.

9. The packaged system of claim 1 wherein:
   the introducer comprises a first introducer and the marker comprises a first marker in the first introducer, the casing comprises a first casing, and the resonating circuit comprises a first resonating circuit configured to produce a wirelessly transmitted first target signal at a first frequency in response to a first excitation signal;
   the system further comprising a second introducer in the package and a second marker in the second introducer, the second marker comprising a second casing configured to be implanted in a patient and a second resonating circuit in the second casing, and the second resonating circuit being configured to wirelessly transmit a second target signal at a second frequency in response to a second excitation signal; and
   the system further comprising a third introducer in the package and a third marker in the third introducer, the third marker comprising a third casing configured to be implanted in a patient and a third resonating circuit in the third casing, and the third resonating circuit being configured to wirelessly transmit a third target signal at a third frequency in response to a third excitation signal.

10. The system of claim 1 wherein the introducer has a lumen, a distal tip, and a projection projecting into the lumen at the distal tip to releasably retain the marker in the lumen during storage.

11. The system of claim 1 wherein:
    the introducer further comprises a handle;
    the stylet has a proximal section fixed to the handle and a distal section projecting from the handle;
    the cannula has a proximal portion and a distal portion, the proximal portion of the cannula being slidably receivable in the handle and slidably positioned over the stylet, and the cannula being slidable through the handle and over the stylet between a storage position in which the distal portion of the cannula extends beyond the stylet and a release position in which at least a length of the distal portion of the cannula is positioned over the stylet; and the marker is retained in the length of the distal portion of the cannula in the storage position.

12. The system of claim 1 wherein the marker does not have external leads projecting externally of the casing.

13. The system of claim 1 wherein the marker further comprises a capacitor electrically coupled to the coil and a ferromagnetic element positioned at least partially within the coil, and wherein the ferromagnetic element has a diameter not greater than approximately 0.7 mm.

14. The packaged system of claim 1 wherein:

the introducer comprises a first introducer having a first handle, the cannula comprises a first cannula of the first introducer having a portion slidably receivable in the first handle, and the stylet comprises a first stylet of the first introducer fixedly attached to the first handle and slidably received in the first cannula, and the system further comprises a second introducer having a second handle, a second cannula having a portion slidably received in the second handle, and a second stylet fixedly attached to the second handle and slidably received in the second cannula;

the marker comprises a first marker in the first cannula of the first introducer, the first marker having a first resonating circuit configured to produce a wirelessly transmitted first target signal at a first frequency in response to a first excitation signal; and the system further comprises a second marker in the second cannula of the second introducer, the second marker comprising a second resonating circuit configured to wirelessly transmit a second target signal at a second frequency in response to a second excitation signal.

15. A packaged system for implanting markers in a patient, comprising:

a plurality of introducers including a first introducer having a first cannula and a first stylet configured to be received in the first cannula, and a second introducer having a second cannula and a second stylet configured to be received in the second cannula;

a first marker in the first cannula, the first marker having a first casing configured to be implanted in a patient and a first resonating circuit in the first casing, and the first resonating circuit being configured to be energized by a wirelessly transmitted first excitation signal and produce a wirelessly transmitted first target signal in response to the first excitation signal;

a second marker in the second cannula, the second marker having a second casing configured to be implanted in the patient and a second resonating circuit in the second casing, and the second resonating circuit being configured to be energized by a wirelessly transmitted second excitation signal and produce a wirelessly transmitted second target signal in response to the second excitation signal; and a package having a sterile compartment, wherein the first and second introducers are contained in the sterile compartment.

16. The packaged system of claim 15 wherein the package comprises a tray and a cover sealed to the tray, the tray having a first introducer retainer in which the first introducer is positioned and a second introducer retainer in which the second introducer is positioned.

17. The system of claim 15 wherein the first introducer has a lumen, a distal tip, and a projection projecting into the lumen at the distal tip to releasably retain the first marker in the lumen during storage.

18. The system of claim 15 wherein:

the first introducer further comprises a handle;

the first stylet has a proximal section fixed to the handle and a distal section projecting from the handle;

the first cannula has a proximal portion and a distal portion, the proximal portion of the first cannula being slidably receivable in the handle and slidably positioned over the first stylet, the first cannula being slidable through the handle and over the first stylet between a storage position in which the distal portion of the first cannula extends beyond the first stylet and a release position in which at least a length of the distal portion of the first cannula is over the first stylet; and the first marker is retained in the length of the distal portion of the first cannula in the storage position.

19. The packaged system of claim 15 wherein the first target signal has a first frequency and the second target signal has a second frequency different than the first frequency.

20. The system of claim 15 wherein the first marker further comprises a capacitor electrically coupled to the coil and a ferromagnetic element positioned at least partially within the coil, and wherein the ferromagnetic element has a diameter not greater than approximately 0.7 mm.

21. A packaged system for implanting markers in a patient, comprising:

an introducer having a cannula and a stylet configured to be received in the cannula;

a plurality of markers in the cannula, the markers including a first marker having a first casing configured to be implanted in a patient and a first resonating circuit in the first casing, the first resonating circuit comprising a first coil configured to wirelessly transmit a first target signal in response to a wirelessly transmitted first excitation signal, and the markers including a second marker having a second casing configured to be implanted in the patient and a second resonating circuit in the second casing, the second resonating circuit comprising a second coil configured to wirelessly transmit a second target signal in response to a wirelessly transmitted second excitation signal;

a spacer in the cannula between the first marker and the second marker; and a package having a sterile compartment, wherein the introducer is contained in the sterile compartment.

22. The packaged system of claim 21, wherein the first target signal has a first frequency and the second target signal has a-second frequency different than the first frequency.

23. The packaged system of claim 21, further comprising a second introducer in the package and a third marker in the second introducer, the third marker comprising a third casing and a third resonating circuit in the third casing, the third resonating circuit comprising a third coil configured to wirelessly transmit a third target signal in response to a wirelessly transmitted third excitation signal.

24. The packaged system of claim 21 wherein the package comprises a tray and a cover sealed to the tray, the tray having an introducer retainer in which the first introducer is positioned.

25. The system of claim 21 wherein:

the introducer further comprises a handle;

the stylet has a proximal section fixed to the handle and a distal section projecting from the handle;

the cannula has a proximal portion and a distal portion, the proximal portion of the cannula being slidably receivable in the handle and slidably positioned over the stylet, and the cannula being slidable through the handle and over the stylet between a storage position in which the distal portion of the cannula extends beyond the stylet and a release position in which at least a length of the distal portion of the cannula is over the stylet; and the first and second markers are retained in the length of the distal portion of the cannula in the storage position.

26. The system of claim 21 wherein the first and second markers do not have external leads projecting externally of the casing.

27. The system of claim 21 wherein the first marker further comprises a capacitor electrically coupled to the first coil and a ferromagnetic element positioned at least partially within the first coil, and wherein the ferromagnetic element has a diameter not greater than approximately 0.7 mm.

\* \* \* \* \*

UNITED STATES PATENT AND TRADEMARK OFFICE
CERTIFICATE OF CORRECTION

PATENT NO.   : 6,889,833 B2
DATED        : May 10, 2005
INVENTOR(S)  : Keith Seiler et al.

It is certified that error appears in the above-identified patent and that said Letters Patent is hereby corrected as shown below:

Column 1,
Line 38, "patent" should be -- patient --;

Column 4,
Line 57, "patent" should be -- patient --;

Column 9,
Line 36, delete "0" between "marker" and "comprises";

Column 12,
Line 55, "a-second" should be -- a second --.

Signed and Sealed this

Eighteenth Day of October, 2005

JON W. DUDAS
*Director of the United States Patent and Trademark Office*